United States Patent [19]

Schroeder et al.

[11] Patent Number: 5,478,948
[45] Date of Patent: Dec. 26, 1995

[54] BENZIMIDAZOLES AND THEIR USE AS CHARGER STABILIZERS

[75] Inventors: Gunter-Rudolf Schroeder, Heidelberg; Udo Mayer, Frankenthal, both of Germany

[73] Assignee: BASF Aktiengesellschaft, Ludwigshafen, Germany

[21] Appl. No.: 116,969

[22] Filed: Sep. 7, 1993

[30] Foreign Application Priority Data

Sep. 29, 1992 [DE] Germany .................. 42 32 524.2

[51] Int. Cl.[6] ............... C07D 235/12; C07D 235/08; G03G 9/08
[52] U.S. Cl. ............... 548/302 V; 430/110; 546/121; 548/420
[58] Field of Search ............... 548/302.4, 720; 430/110; 546/121

[56] References Cited

U.S. PATENT DOCUMENTS

| | | | |
|---|---|---|---|
| 4,212,644 | 7/1980 | Degen et al. | 8/506 |
| 4,265,990 | 5/1981 | Stolka et al. | 430/59 |
| 4,912,006 | 3/1990 | Breitschaft | 430/110 |

FOREIGN PATENT DOCUMENTS

| | | | |
|---|---|---|---|
| 0347695 | 12/1989 | European Pat. Off. | |
| 2733468 | 2/1979 | Germany | 8/506 |

OTHER PUBLICATIONS

Patent Abstracts of Japan, vol. 16, No. 431 (C–983) (5474), Sep. 9, 1992, JP–4–149180, May 22, 1992 (with English specification).

*Primary Examiner*—Floyd D. Higel
*Attorney, Agent, or Firm*—Oblon, Spivak, McClelland, Maier & Neustadt

[57] ABSTRACT

Benzimidazoles of the formula

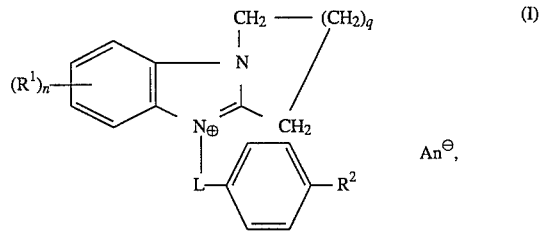

where n and q independently of one another are each 1 or 2, $R^1$ is hydrogen, chlorine or methyl, $R^2$ is hydrogen, unsubstituted or substituted $C_1$–$C_4$-alkyl, halogen, nitro or $C_1$–$C_4$-alkanoyl, L is $C_2$–$C_6$-alkylene and $An^S$ is one equivalent of an anion, are used as charge stabilizers in electrostatic toners.

11 Claims, No Drawings

BENZIMIDAZOLES AND THEIR USE AS CHARGER STABILIZERS

The present invention relates to novel benzimidazoles of the formula I

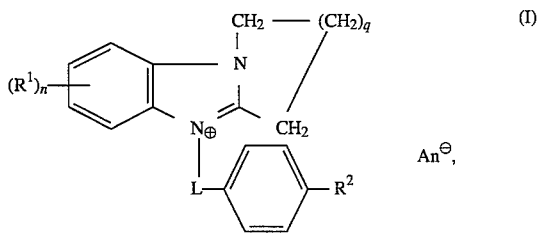

where n and q independently of one another are each 1 or 2, $R^1$ is hydrogen, chlorine or methyl, $R^2$ is hydrogen, unsubstituted or hydroxyl- or $C_1$–$C_4$-alkoxy-substituted $C_1$–$C_4$-alkyl, halogen, nitro or $C_1$–$C_4$-alkanoyl, L is $C_2$–$C_6$-alkylene and $An^\ominus$ is one equivalent of an anion, electrostatic toners containing the benzimidazoles as charge stabilizers and the use of the benzimidazoles as charge stabilizers.

DE-A-2 733 468 and U.S. Pat. No. 4,912,006 disclose similar benzimidazole compounds. However, it has been found that they still have poor performance characteristics when used as charge stabilizers in electrostatic toners.

It is an object of the present invention to provide novel benzimidazoles which have advantageous performance characteristics.

We have found that this object is achieved by the benzimidazoles of the formula I which are defined at the outset.

All alkyl or alkylene groups occurring in the formula I may be either straight-chain or branched.

$R^2$ is, for example, methyl, ethyl, propyl, isopropyl, butyl, isobutyl, sec-butyl, 2-hydroxyethyl, 2- or 3-hydroxypropyl, 2- or 4-hydroxybutyl, 2-methoxyethyl, 2- or 3-methoxylpropyl, 2- or 4-methoxybutyl, 2-ethoxyethyl, 2- or 3-ethoxypropyl, 2- or 4-ethoxybutyl, fluorine, chlorine, bromine, formyl, acetyl, propionyl, butyryl or isobutyryl.

L is, for example, $(CH_2)_2$, $(CH_2)_3$, $(CH_2)_4$, $(CH_2)_5$, $(CH_2)_6$, $CH(CH_3)CH_2$ or $CH(CH_3)CH(CH_3)$.

Examples of suitable anions are inorganic or organic anions, for example halides, such as fluoride, chloride, bromide or iodide, hexafluorophosphate, tetrafluoborate, formate, acetate, propionate, oxalate, benzenesulfonate, toluenesulfonate and tetraphenylboranate.

Preferred benzimidazoles of the formula I are those in which q is 1, $R^1$ is hydrogen, $R^2$ is hydrogen or $C_1$–$C_4$-alkyl, L is $C_3$–$C_6$-alkylene and n and $An^\ominus$ each have the abovementioned meanings.

Benzimidazoles of the formula I where L is $C_3$- or $C_4$-alkylene are of particular interest.

The benzimidazole of the formula Ia

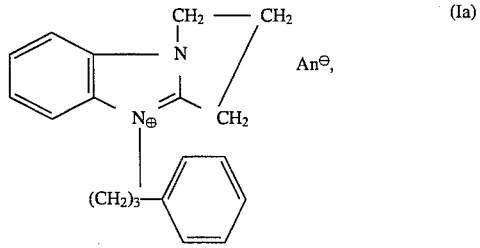

where $An^\ominus$ has the abovementioned meanings is particularly noteworthy.

The novel benzimidazoles of the formula I can be obtained by conventional methods, as described in, for example, DE-A-2 733 468.

For example, a bridged benzimidazole of the formula II

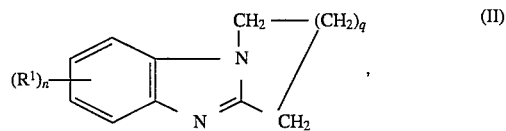

where n, q and $R^1$ each have the abovementioned meanings, can be reacted with a compound of the formula III

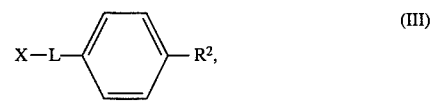

where L and $R^2$ each have the abovementioned meanings and X is a leaving group, eg. chlorine, bromine or iodine, and, if required, then precipitated by means of a salt of the formula IV

where $An^\ominus$ has the abovementioned meanings and $M^\oplus$ is one equivalent of a metal cation, eg. sodium or potassium.

The novel benzimidazoles can be advantageously used as charge stabilizers in electrostatic toners.

The present invention accordingly also relates to electrostatic toners containing a polymeric binder and a benzimidazole of the formula I as a charge stabilizer.

The amount of benzimidazoles of the formula I in the electrostatic toner is as a rule from 0.01 to 10% by weight, based on the weight of the toner.

The polymeric binders present in the novel electrostatic toners are known per se. They are as a rule thermoplastic and have a softening point of from 40° to 200° C., preferably from 50° to 130° C., in particular from 65° to 115° C. Examples of polymeric binders are polystyrene, copolymers of styrene with an acrylate or methacrylate, copolymers of styrene with butadiene and/or acrylonitrile, polyacrylates, polymethacrylates, copolymers of an acrylate or methacrylate with vinyl chloride or vinyl acetate, polyvinyl chloride, copolymers of vinyl chloride with vinylidene chloride, copolymers of vinyl chloride with vinyl acetate, polyester resins, epoxy resins, polyamides or polyurethanes.

In addition to the abovementioned benzimidazoles I and the polymeric binders, the novel toners may contain known amounts of colorants, magnetically attractable material, waxes and fluxes.

The colorants may be organic dyes or pigments, such as nigrosine, Aniline Blue, 2,9-dimethylquinacridone, C.I. Disperse Red 15 (C.I. 6010), C.I. Solvent Red 19 (C.I. 26,050), C.I. Pigment Blue 15 (C.I. 74,160), C.I. Pigment Blue 22 (C.I. 69,810)or C.I. Solvent Yellow 16 (C.I. 12,700), or inorganic pigments, such as carbon black, red lead, yellow lead oxide or chrome yellow. In general, the amount of the colorant present in the toner does not exceed 15% by weight, based on the weight of the toner.

The magnetically attractable material may be, for example, iron, nickel, chromium oxide, iron oxide or a ferrite of the formula $MeFe_2O_4$, in which Me is a divalent metal, eg. iron, cobalt, zinc, nickel or manganese.

The novel toners are prepared by conventional methods, for example by mixing of the components in a kneader and subsequent pulverization or by melting of the polymeric binder or of a mixture of the polymeric binder, subsequent fine division of one or more benzimidazoles I and of the other additives, if used, in the molten resin using the mixing and heading apparatuses known for this purpose, subsequent cooling of the melt to form a solid mass and, finally, milling of the solid mass to give particles of the desired size (as a rule from 0.1 to 50 μm). It is also possible to suspend the polymeric binder and the charge stabilizer in a common solvent and to add the other additives to the suspension. The suspension can thus be used as a liquid toner.

However, it is also possible for the liquid to be spray-dried in a known manner, the solvent to be evaporated off or the liquid freeze-dried and the solid residue milled to give particles of the desired size.

It is also possible for the novel benzimidazoles used as charge stabilizers not to be dissolved but to be finely dispersed in the solution of the polymeric binder. The toner formulation thus obtained can then be used, for example according to U.S. Pat. No. 4,265,990, in a xerographic image recording system.

The abovementioned benzimidazoles of the formula I are advantageous charge stabilizers. In particular, when added to a toner preparation, they impart to the latter an advantageous electrostatic charge build-up profile, ie. the toners can be charged rapidly onto a high charge level. The novel charge stabilizers also ensure that the charge is kept constant at a high level.

The Examples which follow illustrate the invention.

A) Preparation of the benzimidazoles

EXAMPLE H1

79 g of pyrrolidino[1,2-a]benzimidazole and 99.6 g of 1-bromo-3-phenylpropane were stirred for 4 hours at 140° C. The hot melt was then introduced into 1,300 ml of water, a clear dark solution being formed. 60.4 g of sodium tetrafluoborate were added at 60° C. The resulting precipitate was filtered off, recrystallized from isopropanol and dried. 159.5 g of the compound of the formula

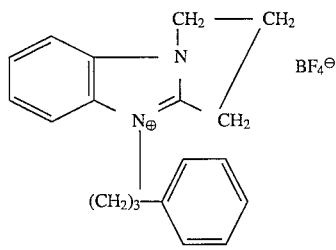

were obtained.

Analysis: C 62.6% (calculated 62.6%) H 5.9% (calculated 5.8%) N 7.7% (calculated 7.7%)

The following benzimidazoles of the formula

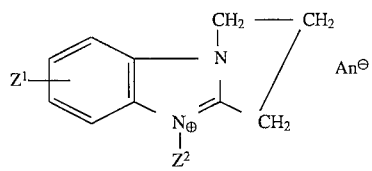

are obtained in a similar manner.

| Bsp. Nr. | $Z^1$ | $Z^2$ | $An^{\ominus}$ |
|---|---|---|---|
| H2 | $CH_3$ | $(CH_2)_3$—C₆H₅ | $BF_4^{\ominus}$ |
| H3 | H | $(CH_2)_4$—C₆H₅ | $BF_4^{\ominus}$ |
| H4 | $CH_3$ | $(CH_2)_4$—C₆H₅ | $BF_4^{\ominus}$ |
| H5 | H | $(CH_2)_3$—C₆H₅ | $Br^{\ominus}$ |
| H6 | H | $(CH_2)_3$—C₆H₄—$NO_2$ | $BF_4^{\ominus}$ |
| H7 | H | $(CH_2)_2$—C₆H₅ | $BF_4^{\ominus}$ |

B) Use

The examples of use were carried out using colorant-free model toners consisting of resin and the novel charge stabilizers.

I. Preparation of the toners

EXAMPLE A1

0.2 g of the benzimidazole of Example H1 was introduced into a solution of 10 g of an uncrosslinked styrene/butyl acrylate resin in 100 ml of xylene at room temperature, and the mixture was then freeze-dried.

EXAMPLE A2

10 g of an uncrosslinked styrene/butyl acrylate resin and 0.2 g of the benzimidazole from Example H1 were thoroughly mixed in a mixer, and headed at 120° C., extruded and milled. Toner particles having a mean particle size of 15 μm were produced by screening.

II. Preparation of the developers and testing

For the preparation of a developer, 99% by weight of a steel carrier which had a mean particle size of 50 μm were accurately weighed in together with 1% by weight of the toner and were activated for a time period as indicated below in a roller stand. The electrostatic charge build-up of the developer was then determined. About 5 g of the activated developer were introduced by means of a commercial q/m meter (from Epping GmbH, Neufahrn) into a hard-blow-off cell which was electrically connected to an electrometer. The mesh size of the screens used in the measuring cell was 50 μm.

This ensured that the toner was as far as possible completely blown off but the carrier remained in the measuring cell. The toner was virtually completely removed from the carrier particles by means of a powerful current (about 4,000 cm³/min) and a simultaneous extraction, the carrier particles remaining in the measuring cell. The charge buil-up on the carrier was recorded on the electrometer. It corresponded to the magnitude of the charge build-up on the toner particles, but with the opposite sign. To calculate the q/m value, the magnitude of q was therefore used with the opposite sign. The mass of blown-off toner was determined by reweighing the measuring cell, and the electrostatic charge q/m was calculated therefrom.

The charge build-up determined on the toners is summarized in the Table below.

TABLE

| Example No. | Compound from Example | Charge build-up after activation for | | | |
|---|---|---|---|---|---|
| | | 10 min | 30 min | 60 min | 120 min |
| | | | | [μC/g] | |
| A1 | H1 | 6,1 | 5,7 | 5,6 | 5,2 |
| A2 | H2 | 6,5 | 6,0 | 6,0 | 5,7 |
| A3 | H3 | 5,2 | 5,0 | 5,0 | 4,9 |
| A4 | H4 | 5,4 | 4,9 | 4,7 | 4,5 |
| A5 | H5 | 6,0 | 5,5 | 5,6 | 5,3 |
| A6 | H7 | 5,8 | 4,6 | 4,6 | 3,8 |

We claim:

1. A benzimidazole of the formula I

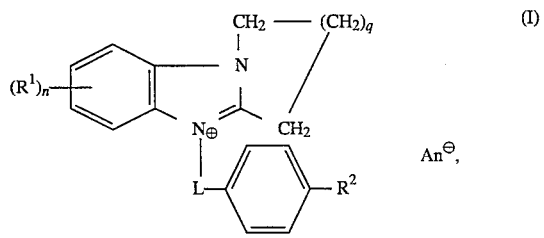

where n and q independently of one another are each 1 or 2, $R^1$ is hydrogen, chlorine or methyl, $R^2$ is hydrogen, unsubstituted, hydroxyl- or $C_1$–$C_4$-alkoxy-substituted $C_1$–$C_4$-alkyl, halogen, nitro or $C_1$–$C_4$-alkanoyl, L is $C_3$–$C_6$-alkylene and $An^\ominus$ is an anion.

2. The benzimidazole as claimed in claim 1, wherein q is 1, $R^1$ is hydrogen, $R^2$ is hydrogen or $C_1$–$C_4$-alkyl and L is $C_3$–$C_6$-alkylene.

3. The benzimidazole as claimed in claim 1, wherein L is $C_3$–$C_4$-alkylene.

4. The benzimidazole as claimed in claim 1, wherein $R^2$ is unsubstituted, hydroxyl or $C_1$–$C_4$-alkoxy-substituted $C_1$–$C_4$ alkyl, halogen, nitro or $C_1$–$C_4$-alkanoyl.

5. The benzimidazole as claimed in claim 1, wherein L is $C_3$-alkylene.

6. The benzimidazole as claimed in claim 1, wherein L is $C_4$-alkylene.

7. The benzimidazole as claimed in claim 1, wherein L is $C_5$-alkylene.

8. The benzimidazole as claimed in claim 1, wherein L is $C_6$-alkylene.

9. A benzimidazole of the formula I

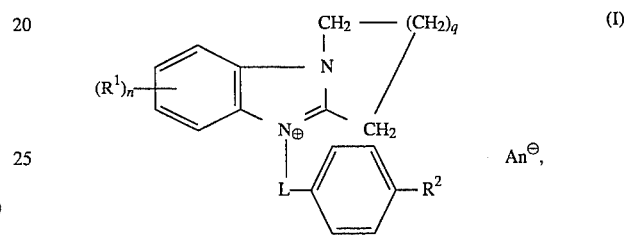

where n and q independently of one another are each 1 or 2, $R^1$ is hydrogen, chlorine or methyl, $R^2$ is unsubstituted, hydroxyl- or $C_1$–$C_4$-alkoxy-substituted $C_1$–$C_4$-alkyl, halogen, nitro or $C_1$–$C_4$-alkanoyl, L is $C_3$–$C_6$-alkylene and $An^\ominus$ is an anion.

10. An electrostatic toner containing a polymeric binder and, as a charge stabilizer, a benzimidazole as claimed in claim 1.

11. A method of stabilizing a charge in electrostatic toners using the benzimidazole as claimed in claim 1.

* * * * *